(12) United States Patent
Melapudi et al.

(10) Patent No.: US 11,850,090 B2
(45) Date of Patent: Dec. 26, 2023

(54) GUIDED LUNG COVERAGE AND AUTOMATED DETECTION USING ULTRASOUND DEVICES

(71) Applicant: GE Precision Healthcare LLC, Wauwatosa, WI (US)

(72) Inventors: Vikram Melapudi, Bangalore (IN); Chandan Kumar Mallappa Aladahalli, Bangalore (IN); Krishna Seetharam Shriram, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 513 days.

(21) Appl. No.: 17/029,858

(22) Filed: Sep. 23, 2020

(65) Prior Publication Data

US 2022/0087645 A1    Mar. 24, 2022

(51) Int. Cl.
*A61B 8/00* (2006.01)
*A61B 8/08* (2006.01)
(Continued)

(52) U.S. Cl.
CPC .......... *A61B 8/4263* (2013.01); *A61B 8/4245* (2013.01); *A61B 8/463* (2013.01);
(Continued)

(58) Field of Classification Search
CPC ....... A61B 8/5223; A61B 8/42; A61B 8/4245; A61B 8/4263; A61B 8/461–466; G06T 7/0012; G06T 7/70; G06T 2207/30061
See application file for complete search history.

(56) References Cited

U.S. PATENT DOCUMENTS

2017/0105701 A1*  4/2017  Pelissier ................ A61B 8/565
2020/0054306 A1*  2/2020  Mehanian .............. G16H 30/40
(Continued)

OTHER PUBLICATIONS

Volpicelli et al., "International evidence-based recommendations for point-of-care lung ultrasound," Intensive Care Med 38, 577-591 (2012), [https://doi.org/10.1007/s00134-012-2513-4], 15 pages.
(Continued)

*Primary Examiner* — Colin T. Sakamoto
*Assistant Examiner* — Tommy T Ly

(57) ABSTRACT

Systems and methods for guided lung coverage and automated detection using ultrasound devices are disclosed. The method for guided coverage and automated detection of pathologies of a subject includes positioning an ultrasound probe on a region of the subject body to be imaged. The method includes capturing a video of the subject and processing the video to generate a torso image of the subject and identify location of the ultrasound probe on the subject body. The method includes registering the video to an anatomical atlas to generate a mask of the region of the subject body comprising a plurality of sub-regions of the subject body to be imaged and superimposing the mask over the torso image. The method further includes displaying an indicator corresponding to a location of the each of the plurality of the sub-regions on the torso image. The method further includes displaying the relative position of the ultrasound probe with respect to the indicator corresponding to the location of the each of the plurality of plurality of sub-regions of the subject body to be imaged.

22 Claims, 8 Drawing Sheets

(51) Int. Cl.
    *G06T 7/00* (2017.01)
    *G06T 7/70* (2017.01)
    *G06T 11/00* (2006.01)
    *G06V 10/10* (2022.01)

(52) U.S. Cl.
    CPC .......... *A61B 8/5223* (2013.01); *G06T 7/0012* (2013.01); *G06T 7/70* (2017.01); *G06T 11/00* (2013.01); *G06V 10/17* (2022.01); *G06T 2207/10016* (2013.01); *G06T 2207/10132* (2013.01); *G06T 2207/30061* (2013.01)

(56) References Cited

U.S. PATENT DOCUMENTS

| | | | |
|---|---|---|---|
| 2020/0054307 A1* | 2/2020 | Silberman | A61B 8/4427 |
| 2020/0069291 A1* | 3/2020 | Zaslavsky | A61B 8/4245 |
| 2020/0194117 A1* | 6/2020 | Krieger | A61B 8/429 |

OTHER PUBLICATIONS

Cao et al., "OpenPose: Realtime Multi-Person 2D Pose Estimation using Part Affinity Fields," higharXiv: 1812.08008v2 [cs.CV] May 30, 2019, [https://arxiv.org/abs/1812.08008], 14 pages.

* cited by examiner

GUIDED LUNG COVERAGE AND AUTOMATED DETECTION USING ULTRASOUND DEVICES

FIELD OF THE INVENTION

This disclosure relates generally to improved medical imaging systems and methods, and more particularly to systems and methods for guided lung coverage and automated detection of the pathologies by adjusting the ultrasound probe position on the subject body.

BACKGROUND OF THE INVENTION

Various medical imaging systems and methods are used to obtain the images of the affected regions of the subject for diagnosing the medical condition. Ultrasound imaging is a known medical imaging technique used for imaging the different body parts like joints, muscles vessels and pregnant woman (known as obstetric ultrasound). Ultrasound imaging offers several advantages over the other imaging techniques as ultrasound is a real-time imaging technique that provides live stream of images. Commercially, the ultrasound devices are available in various configurations and the portable ultrasound devices are used for capturing the relatively bigger regions of the subject anatomy like uterus, lower abdominal portions and lungs.

Ultrasound imaging involves generating and sending the ultrasound waves towards the portion of the subject body to be imaged and receiving the reflected waves from the subject body. Ultrasound imaging device consists of a probe that may be positioned on the skin of the subject over the portion of the pathology to be imaged. The probe emits the ultrasound waves into the body of the subject and the reflected waves may be captured to generate an image of the pathology of the subject.

A user viewable ultrasound image is formed using the known image processing techniques. However, a skilled operator is required for accurate imaging of the subject using the portable ultrasound devices. Any error on part of the operator would result in an image containing excessive disturbance or noise. Therefore, training of the operator and her experience in handling the ultrasound imaging devices will affect the ultrasound image quality. The operator may be skilled in acquiring the good quality images of the certain portion of the body due to her experience in obtaining the images of that body portion, but the operator may not be skilled to obtain the high-quality images of the entire subject body. This may be due to the lack of the imaging experience or lack of the anatomical knowledge of the entire body. Also, placing the ultrasound probe at the appropriate body portion affects the quality of the image. Physical parameters of the subject body like obesity, bone density, height, chest or abdominal size will create a challenging situation for the operator to correctly position the ultrasound probe for obtaining the complete image of the region of interest. Any wrong placement of the ultrasound probe would result in incomplete imaging of the regions of interest.

Coronavirus disease (COVID-19) as defined by the World Health Organization (WHO) is an infectious disease caused by a newly discovered coronavirus. One of the conditions that is often observed in COVID-19 infected subjects is infection of the lungs and in severe cases pneumonia. Frequent imaging is recommended to monitor the progress of the COVID19 infection. It is therefore important to obtain better quality ultrasound images of the subject that will provide valuable information about the progress of the COVID-19 disease. Rapid response to pandemics has become and will be an acute need going forward. Ultrasound provides a quick diagnosis of the lung condition which is especially important for the current COVID-19 pandemic. With a critical shortage of the trained medical personnel, the novice users such as the paramedics and the nurses should be able to quickly assess the lung condition using the ultrasound devices. Lack of scanning expertise in operating the ultrasound devices will result in generating the images with poor quality resulting in poor assessment of the subject condition. This may cause loss of several invaluable lives.

With the outbreak of the Covid-19 pandemic, the healthcare resources worldwide have been stretched to the limits. Rapid screening at a large scale would require the services of the para-medical and other less skilled healthcare workers. Ultrasound has been shown to detect the pleural effusion and the lung consolidation but requires substantial skill on the part of the operator to maneuver the probe. Moreover, the Covid-19 has exhibited certain locational patterns which must be covered by the operator during the triaging process. Covid-19 manifestation is typically multifocal and peripheral often involving the lower lobes. Since the field of view (FoV) of the ultrasound is very limited, it is not possible to know if all the Covid-19 affected portions or hotspots within the lung of a subject have been covered during the lung examination.

Systems and methods are required for providing an automated guidance to the scanning personnel to appropriately position and operate the ultrasound probe to scan regions of the lung of the subject and generate images that would help in tracking the progress of the COVID19 disease.

SUMMARY OF THE INVENTION

This summary introduces concepts that are described in more detail in the detailed description. It should not be used to identify essential features of the claimed subject matter, nor to limit the scope of the claimed subject matter. Its sole purpose is to present concepts in a simplified form as a prelude to the more detailed description that is presented later.

In accordance with an aspect of the disclosure a method is disclosed for guided coverage and automated detection of the pathologies of a subject. The method comprises positioning an ultrasound probe on a region of the subject body to be imaged. The method further comprises capturing a video of the subject body and processing the video to generate a torso image of the subject body and identify location of the ultrasound probe on the subject body. The method further comprises registering the video to an anatomical atlas to generate a mask of the region of the subject body comprising a plurality of sub-regions of the subject body to be imaged and superimposing the mask over the torso image. The method further comprises displaying an indicator corresponding to a location of the each of the plurality of the sub-regions on the torso image. The method further comprises displaying a relative position of the ultrasound probe with respect to the indicator corresponding to the location of the each of the plurality of sub-regions of the subject body to be imaged.

In accordance with an aspect of the disclosure a system is disclosed for guided coverage and automated detection of the pathologies of a subject body. The system comprises a portable device comprising a camera and a display configured to acquire a video of the subject body. The system further comprises an ultrasound probe positioned over a region of the subject body to be imaged and connected to the portable device. The system further comprises a computer system connected to the portable device and configured to receive a plurality of ultrasound images and the video of the subject body. The computer system comprises a processor and a memory connected to the processor. The computer system further comprises at least one artificial intelligence module deployed over the memory and configured to generate a torso image of the subject body. The computer system further comprises an atlas module deployed over the memory and configured generate a mask of the region of the subject body comprising a plurality of sub-regions to be imaged and superimpose the mask over the torso image of the subject body. The computer system is further configured to display an indicator corresponding to a location of the each of the plurality of the sub-regions on the torso image and display a relative position of the ultrasound probe with respect to the indicator corresponding to the location of the each of the plurality of sub-regions of the subject body.

DETAILED DESCRIPTION

Figure 1:
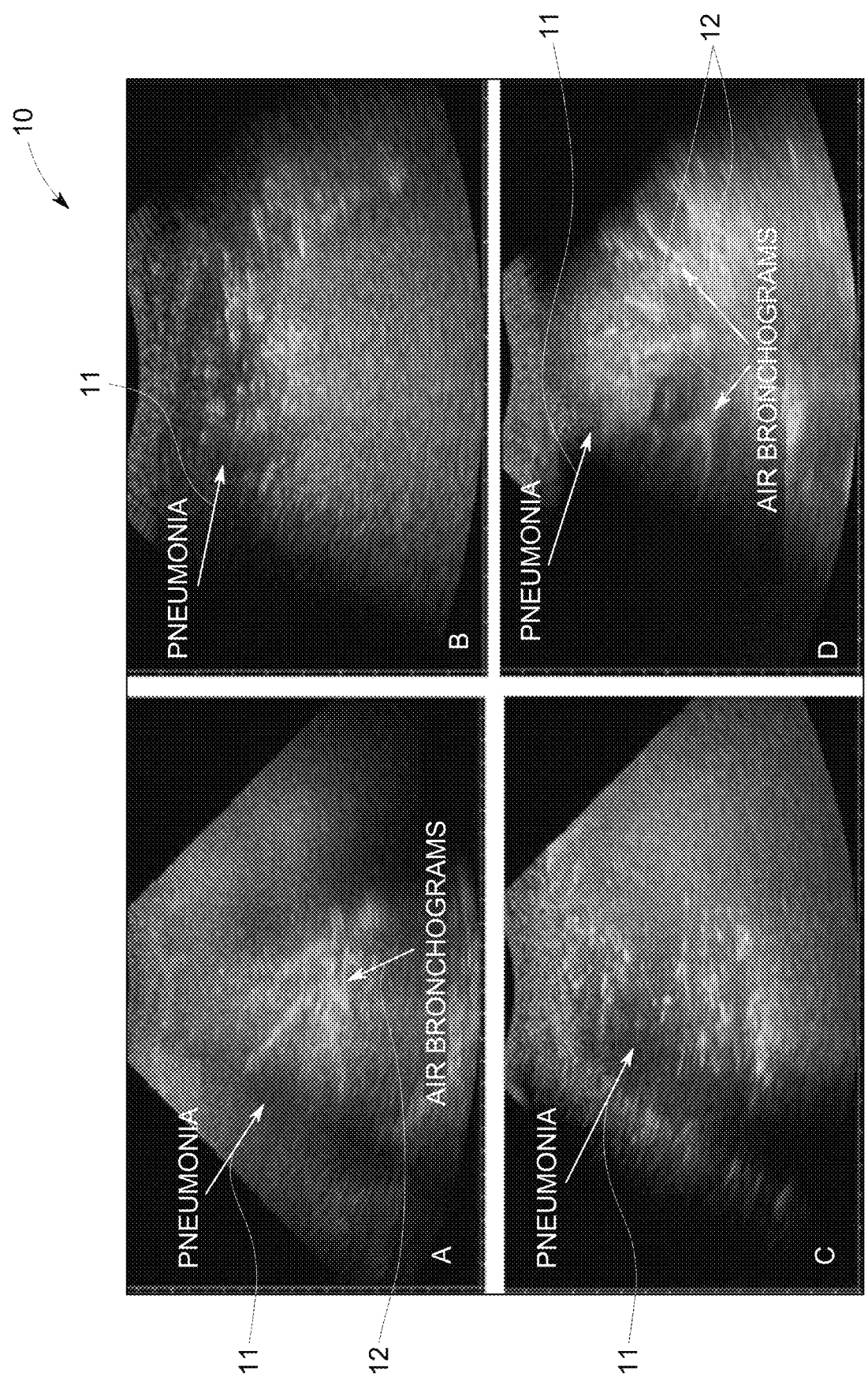
FIG. 1 illustrates an ultrasound image of a subject having a pneumonia like condition according to an aspect of the disclosure.

In the following specification and the claims, reference will be made to a few terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable and include any computer program stored in memory for execution by devices that include, without limitation, mobile devices, clusters, personal computers, workstations, clients, and servers.

As used herein, the term "computer" and related terms, e.g., "computing device", "computer system" "processor", "controller" are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

In one aspect of the disclosure a method is disclosed for guided coverage and automated detection of the pathologies of a subject. The method comprises positioning an ultrasound probe on a region of the subject body to be imaged. The method further comprises capturing a video of the subject body and processing the video to generate a torso image of the subject body and identify location of the ultrasound probe on the subject body. The method further comprises registering the video to an anatomical atlas to generate a mask of the region of the subject body comprising a plurality of sub-regions of the subject body to be imaged and superimposing the mask over the torso image. The method further comprises displaying an indicator corresponding to a location of the each of the plurality of the sub-regions on the torso image. The method further comprises displaying a relative position of the ultrasound probe with respect to the indicator corresponding to the location of the each of the plurality of plurality of sub-regions of the subject body to be imaged.

In another aspect of the disclosure a system is disclosed for guided coverage and automated detection of the pathologies of a subject. The system comprises a portable device comprising a camera and a display configured to acquire a video of the subject body. The system further comprises an ultrasound probe positioned over a region of the subject body to be imaged and connected to the portable device. The system further comprises a computer system connected to the portable device and configured to receive a plurality of ultrasound images and the video of the subject body. The computer system comprises a processor, a memory connected to the processor, at least one artificial intelligence module deployed over the memory and configured to generate a torso image of the subject body. The computer system further comprises an atlas module deployed over the memory and configured generate a mask of the region of the subject body comprising a plurality of sub-regions to be imaged and superimpose the mask over the torso image of the subject body. The computer system is configured to display an indicator corresponding to a location of the each of the plurality of the sub-regions on the torso image and display a relative position of the ultrasound probe with respect to the indicator corresponding to the location of the each of the plurality of sub-regions of the subject body over the display of the portable device.

Embodiments of the present disclosure will now be described, by way of example, with reference to the figures, in which FIG. 1 shows an ultrasound image (10) of a subject (not shown) with symptoms of pneumonia (11) and air bronchogram (12). In Covid-19 cases, pneumonia (11) is one of the important indications of the severe spread of the infection. These symptoms are observed in the peripheral and the lower regions of the lung. When the ultrasound images (10) of the lung are captured, the symptoms of pneumonia may appear as the textural changes in the ultrasound images (10). Capturing the ultrasound images (10) without the expertise required to obtain the entire coverage of the lung may result in missing out some of the affected regions. This may result in an anomaly in the diagnosis of the subject condition.

Figure 2:
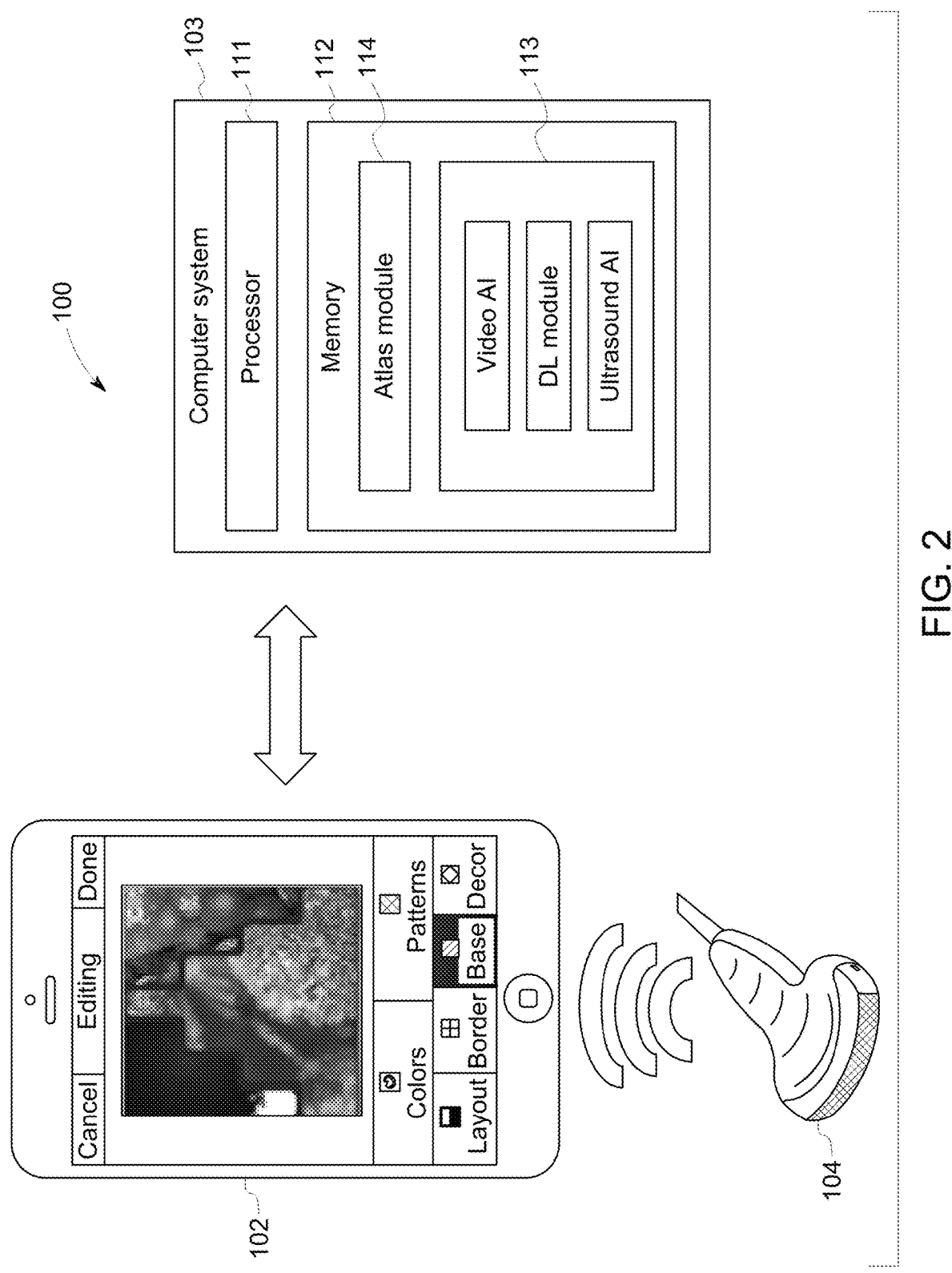
FIG. 2 illustrates a system for guided coverage and automated detection of the pathologies of a subject according to an aspect of the disclosure.

In one aspect of the disclosure, FIG. 2 shows a system (100) for guided coverage and automated detection of the pathologies of subject (101). The system (100) includes a portable device (102) used by the operator to capture a video stream or images of the subject (101). The portable device (102) may be a mobile phone having a camera to capture the video stream or the images of the subject (101) and contains a display screen. A computer system (103) may be connected to the portable device (102) and the video or the live stream from the portable device (102) may be transferred to the computing device (103) for further processing. An ultrasound probe (104) may be configured to obtain the ultrasound images of the subject (101) and the ultrasound probe (104) may be connected to the portable device (102).

The computing device (103) may contain a processor (111), a memory (112), and at least one artificial intelligence module (113) deployed over the memory (112). The artificial intelligence module (113) may be a deep learning module that may be trained to compare the video stream or the images obtained by the mobile camera with the stored images of the subject bodies of the varying shapes, and identify an image that closely matches the actual shape of the subject (101). The artificial intelligence module (113) may be configured to identify and generate a torso image of the subject (101) and landmarks on the image as explained in detail with reference to FIGS. 3 and 4.

The computing device (103) may contain an atlas module (114) configured to register the images or the video stream from the mobile camera. Atlas module (114) registration ensures external scale alignment and may provide the grid lines on the received images. The atlas module (114) may be configured to generate a lung mask containing the grid lines and superimposing the mask on the torso image to indicate a plurality of sub-regions (560) of interest for imaging. The atlas module (114) output containing a plurality of sub-regions (560) may be displayed to the operator over the mobile phone to indicate the sub-regions (560) to be imaged.

Further, the position of the ultrasound probe (104) may be obtained by the mobile camera and indicated to the operator over the mobile device (102) screen. When the ultrasound probe (104) is correctly positioned over at least one of the sub-regions (560) indicated by the atlas module (114), the operator may be given an audio-visual signal to carry out the imaging procedure. Alternatively, when the position of the ultrasound probe (104) over the body of the subject (101) is not matching at least one of the sub-regions (560) indicated by the atlas module (114), another audio-visual signal or an indication may be provided to the operator to change the position of the ultrasound probe (104) to an identified location. Continuous audio-visual indications may be provided to the operator to guide the operator to accurately position the ultrasound probe (104) over at least one of the marked sub-regions (560). When the operator positions the ultrasound probe over at least one of the sub-regions (560) and carries out imaging at the indicated sub-regions (560) of the subject (101), detailed ultrasound images of the pathologies of the subject lung may be obtained.

In one aspect of the disclosure, for faster detection of the developing COVID-19 conditions in the subject (101), the ultrasound images of the subject (101) may be compared with the similar images to identify the severity of the medical condition of the subject. Several ultrasound streams containing the images of the various sub-regions (560) of the lung from different subjects (101) may be used to train an artificial intelligence module (113). In one example, the artificial intelligence module (Ultrasound AI) (113) may be configured to analyze the pathologies to identify spread of the COVID-19 across the various sub-regions (560) of the lung. The artificial intelligence module (113) may be a single module or set of several individual modules trained to execute the functionalities and include for example Deep learning (DL) modules, Convolution Neural Networks, Supervised, Semi-supervised or non-supervised artificial intelligence modules. The ultrasound AI (113) may be used along with the mobile camera to detect the location of the probe (104) and carrying out imaging. If the ultrasound probe (104) is placed at an incorrect position, the ultrasound AI (113) may be configured to send a signal indicating incorrect positioning of the ultrasound probe (104). The ultrasound probe (104) may be moved to a correct position for guided lung coverage, and automatic detection of the pathologies using the artificial intelligence module (113). Guided lung coverage and automatic detection of the pathologies for all the sub-regions (560) indicated on the display screen may be accomplished by the operator.

Deep Learning Module, Machine Learning Module and Artificial Intelligence Network Terms deep learning (DL), machine learning (ML) and artificial intelligence (AI) are correlated and often used interchangeably. However, artificial intelligence is a relatively broader technology that covers intelligent machines with thinking capability and machine learning includes learning from data.

Deep learning is a class of machine learning techniques employing representation learning methods that allows a machine to be given raw data and determine the representations needed for data classification. Deep learning ascertains structure in data sets using backpropagation algorithms. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine operating conditions. A neural network behaves in a certain manner based on its own sequences. Learning refines the machine output, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the system for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as conditions for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is enough for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

Figure 3:
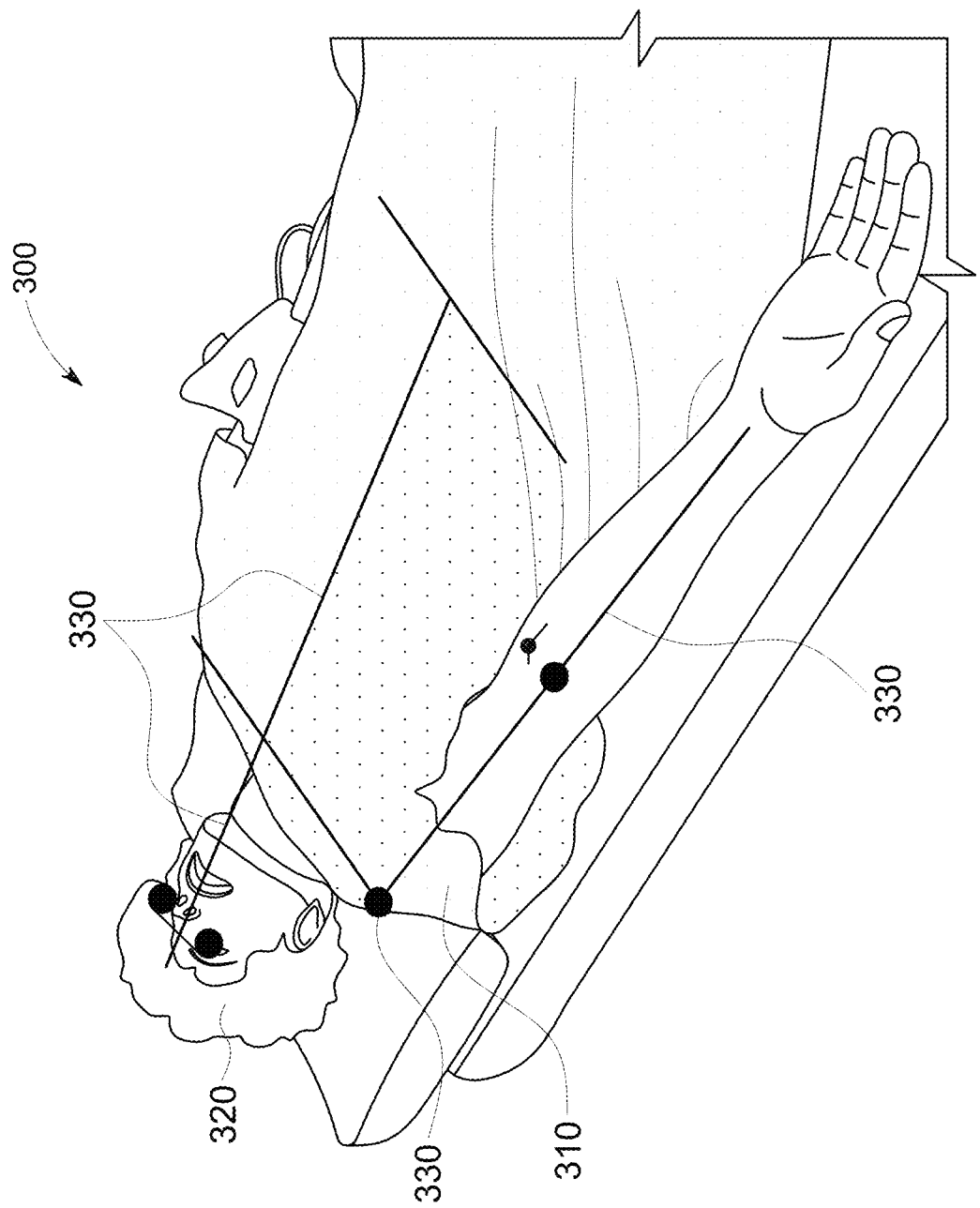
FIG. 3 illustrates an image of the subject obtained using a portable device according to an aspect of the disclosure.

In accordance with an aspect of the disclosure, FIG. 3 shows a torso image (300) of a subject (101) generated using a deep learning (DL) module from the images obtained using the camera of the portable device (102). The portable device (102) may be any known commercially available device with at least one camera that may capture the videos or images of the subject (101). The portable device (102) may be a handheld portable device or a fixed device configured to acquire, store and send images of the subject over a wired or wireless network to the other devices. According to an aspect of the disclosure, the portable device (102) may be a mobile phone with a camera that is capable of being operated simultaneously with the ultrasound probe. During operation of the camera, the mobile phone may be handheld by the operator and the video stream or the images of the subject body may be captured. The mobile phone camera is capable of imaging the larger surface area of the subject body than the ultrasound probe (104).

The video or the images of the subject (101) captured by the mobile phone camera may be sent to the computer memory (112) and stored on the computer memory (112). The video or the images of the subject (101) obtained by the mobile phone camera may be used generate the torso image (310) of the subject (101) and identify location of the ultrasound probe (104) on the subject body (101). The torso image (300) may be a front, back or side view of the subject body (101). A deep learning (hereinafter DL) module (113) may be employed on the computer system (103) for body pose detection for the head (320) or the torso (310). The deep learning module (113) may be trained using the different available body images to identify the head (320) or the torso (310). The images obtained using the mobile phone camera are processed by the DL module (113) to generate the torso image (300) of the subject (101). The DL module may be further configured for body pose estimation. Body pose estimation includes identifying alignment and orientation of various organs of the subject body (101) using the DL module (113). For detecting location of the specific organs and delineating different organs for imaging, the DL module (113) based pose detection may provide landmarks (330) on the subject body. The landmarks (330) may define pose, orientation and boundaries of various organs of the subject body (101). The mobile phone may be further configured to receive the ultrasound images of the subject (101) obtained using the ultrasound probe (104) positioned over the subject body.

Figure 4:
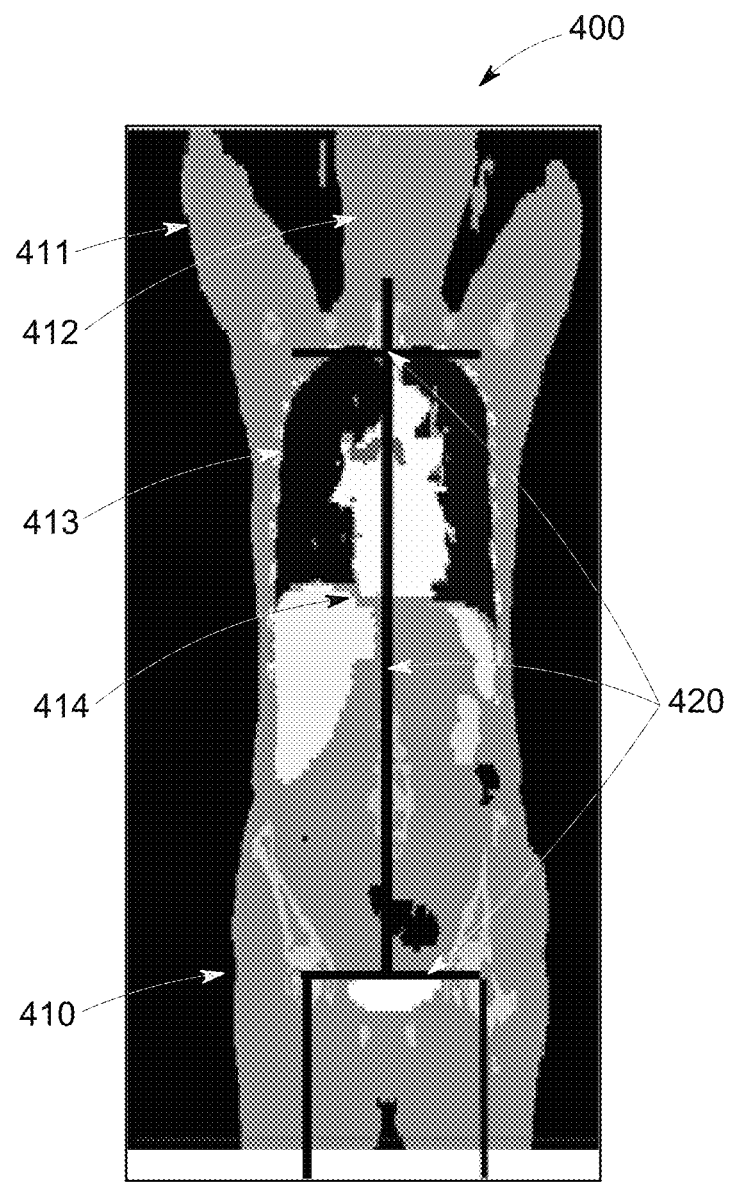
FIG. 4 illustrates an atlas that receives images of the torso and uses external landmarks according to an aspect of the disclosure.

In accordance with an aspect of the disclosure, FIG. 4 shows atlas-based segmentation (400) and registration. Atlas based segmentation of the torso image (410) of the subject body (101) is a technique in medical imaging that is used to delineate the subject organs for example hand (411), head (412), lungs (413) and abdomen (414) from one another and saving the time required by the experts in delineation. An atlas module (114) may be employed over the computer system for segmentation and delineation. The images obtained using the mobile phone camera may be processed by the DL module (113) for body pose detection and sent to the atlas module (114) for segmentation and registration. The atlas module (114) uses the externally detected landmarks (420) by the DL module (113) for segmentation and registration of the images with the atlas module (114). The atlas module (114) may be further configured to generate mask of an organ that may be superimposed over the torso image and display on the mobile phone screen to the operator.

According to an aspect of the disclosure, as shown in FIG. 4 the atlas (400) that receives images of the torso (410) and uses the external landmarks (420) detected by the DL module (113) to register the images with the atlas module (114). The atlas registration ensures the gross pose and the external scale alignment.

Figure 5:
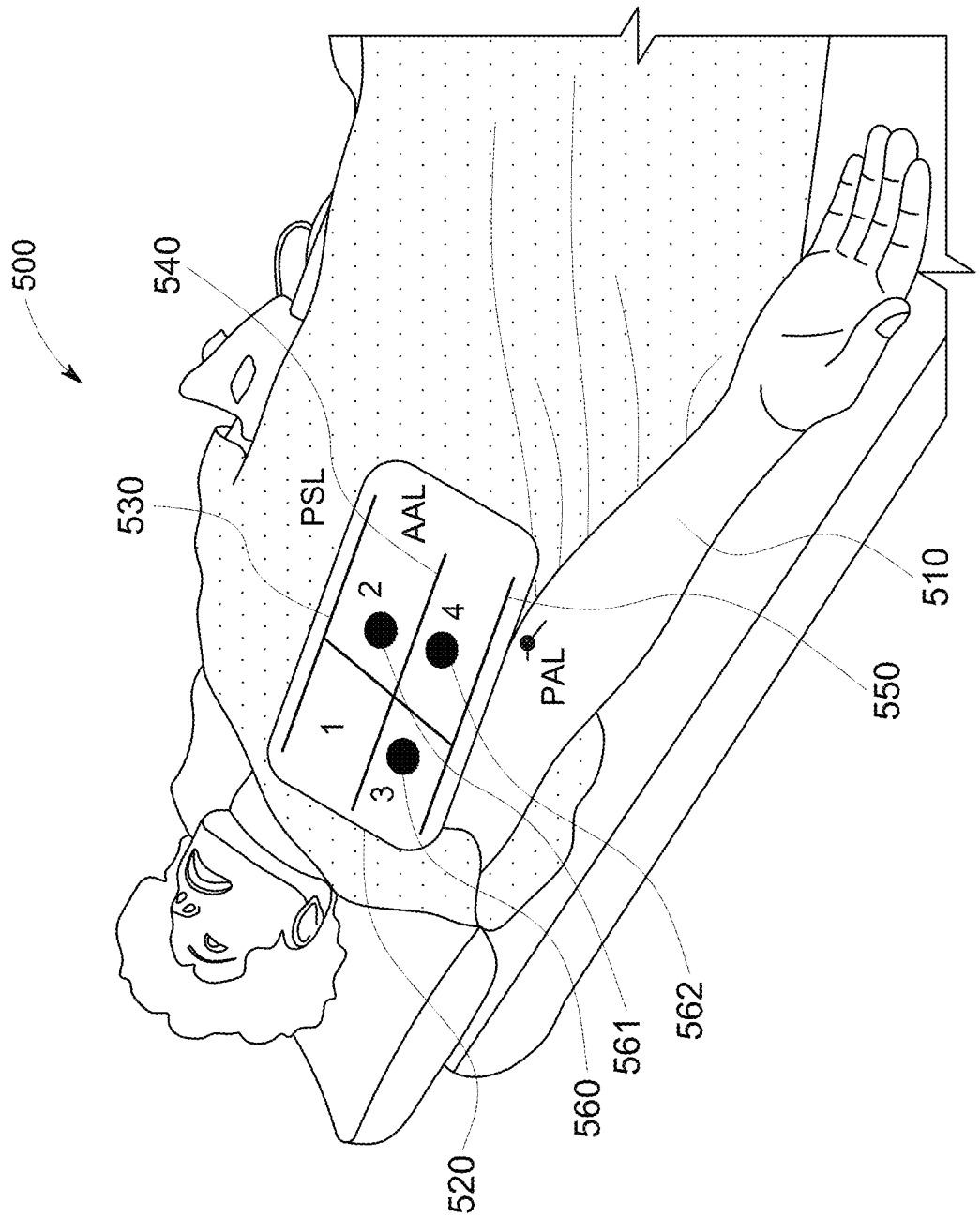
FIG. 5 illustrates a plurality of grid lines generated by the atlas module over the mask of the lower lung region according to an aspect of the disclosure.

In accordance with an aspect of the disclosure, as shown in FIG. 5, the atlas module (114) may be configured to provide a user viewable image (500) of the torso of the subject body (101). The atlas module (114) may be configured to generate the lung mask (520) that may be superimposed over the torso image (510) of the subject body (101) and displayed on the mobile screen. A mask image (520) is an image where some of the pixel intensity values are zero, and others are non-zero. If the pixel intensity value is zero in the mask image (520), then the pixel intensity of the resulting masked image will be set to the background value. Zero mask value represents background areas of the images that are insignificant and do not contain any meaningful information. Pixels containing meaningful information that are inside the mask (520) do not have their pixel values changed and they are left at the same intensity as the input image.

The novice operator may see the video stream of the subject body (101) and the torso image (510), and position of the ultrasound probe (104) on the subject body (101) that may be viewed in one window of the mobile phone screen (102). The mobile phone screen displays the lung mask (520) superimposed over the torso image (510) by the atlas module (114) and the current position of the ultrasound probe (104) on the subject body. Further, the atlas module (114) may be configured to generate a plurality of grid lines (530, 540, 550) over the mask (520) and indicate the position of the lung sub-regions (560) to be imaged. When views of the subject lung, the ultrasound probe placement and the grid lines (530, 540, 550) are available, the operator has all the essential views and controllable parameters available for the complete imaging of the subject lung.

During examination of the various subjects (101), the subjects (101) of various body shapes, sizes and height will appear for imaging. It is important to correctly identify the location of the subject organs on the subject body image and appropriately indicate to the operator for imaging the subject (101). An artificial intelligence module (113) may be trained to identify the location of the various organs on the subject body and display the location of the organ to the operator. The artificial intelligence module (113) may be employed during the video acquisition stage (Video AI) to identify the actual shape of the body and corelate it to the stored images to determine the location of the subject organs. This will supplement the atlas module (114) to more accurately delineate the organs and the grid lines (530, 540, 550).

The atlas module (114) may be configured to provide the grid lines (530, 540, 550) over the mask (520) that define the lower lung region of the subject (101) in greater detail. According to an aspect of the disclosure, the atlas module (114) may insert a parasternal line (530), an anterior axillary line (540) and a posterior axillary line (550) over the mask (520) that mark the lung of the subject body. These grid lines (530, 540, 550) may be displayed over on the mobile phone screen to the operator. Further, the grid lines (530, 540, 550) may divide the mask (120) into portions (1, 2, 3, 4) for more accurately defining the location of different sub-regions (520). The atlas module (114) may further divide the lung area in suitable regions for imaging. The atlas module (114) may be configured to mark the critical zones or the sub-regions (560) of the lung that require detailed imaging. Further, the superimposed grid lines (530, 540, 550) may further divide the lung surface area to precisely define the location of the sub-regions (560) that require detailed imaging. For convenience of the operator of the mobile device (102), the display screen may show only the sub-regions (560) located within the grid lines (530, 540, 550). Further, the each of the sub-regions (560) may be shown by a suitable indicator at a location corresponding to the location of the sub-regions (560). In one example, the indicator corresponding to the sub-region (560) may be the areas (561, 562) shown in red color. According to an aspect of the disclosure, it may not necessary to display the mask (520) to the operator, however, only the indicators (561, 562) corresponding to the location of the sub-regions (560) may be displayed to the operator for imaging. The position of the ultrasound probe (104) may be adjusted to scan the sub-regions (560) marked by the atlas module (114). When the ultrasound probe (104) is correctly positioned to scan the sub-regions (560) indicated by the atlas module (114), a signal may be sent to the operator regarding the accurate positioning of the ultrasound probe (104). When the ultrasound probe (104) is not accurately positioned over the marked sub-regions (560) of the lung, the images may fail to clearly show the pathology of the subject (101). A signal indicating inaccurate positioning of the ultrasound probe (104) may be sent to the operator. The operator may be indicated by the computer system (103) of incorrect positioning of the ultrasound probe (104) and guided to change the position of the ultrasound probe (104) to the marked sub-regions (560) to carry out detailed imaging. In one example, if the ultrasound probe (104) is placed on the right side at three-centimeter (3 cm) distance from the marked sub-region (560), the operator may be guided to move the ultrasound probe (104) towards left side for 3 cm for imaging. Similarly, the operator may be guided to move the ultrasound probe (104) in vertical, lateral or diagonal directions for accurate positioning over the sub-regions (560) or sub-region indicators (561, 562). For a novice operator, displaying the position of the ultrasound probe (104) on the subject body and indicating the location of the sub-regions (560) to be imaged, guides the operator to correctly position the ultrasound probe (104) over the sub-regions (560). The images obtained by accurately positioning the ultrasound probe (104) over the sub-regions (560) are clinically more relevant for diagnosing the pneumonia like condition in the COVID-19 disease.

Further, the accurate placement of the ultrasound probe (104) at the sub-regions (560) indicated by the atlas module (114) on the subject body needs continuous monitoring. Once the ultrasound probe (104) is positioned at a correct location indicated by the atlas module (114), a correlation may be established between the images obtained by the ultrasound probe (104) and the location of the ultrasound probe (104). This correlation helps in determining the location of the COVID-19 pathologies. Further, these ultrasound images may be stored for the future reference to analyze the progress of the COVID-19 disease by comparing the new set of ultrasound images obtained in future with the stored images.

Figure 6:
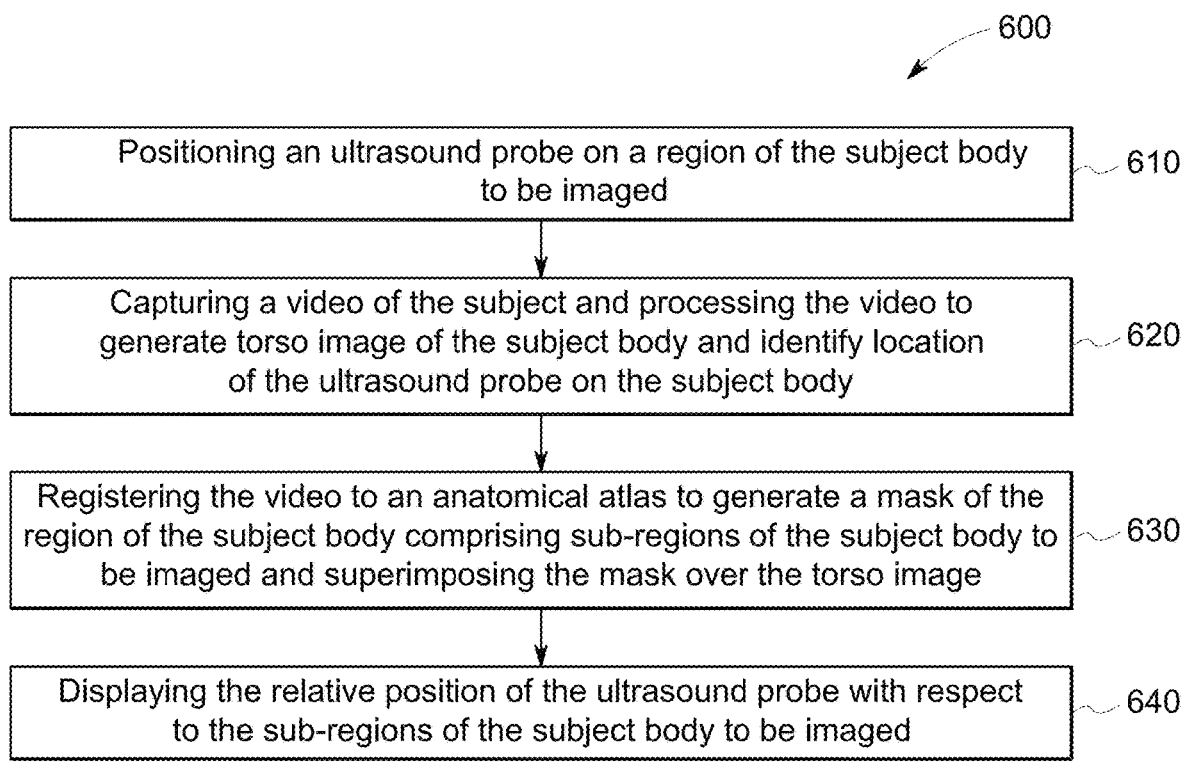
FIG. 6 illustrates a method for guided coverage and automated detection of the pathologies of a subject according to an aspect of the disclosure.

In another aspect of the disclosure, FIG. 6 shows a method (600) for guided lung coverage and automatic detection of the pathologies. The method (600) helps the operator of the ultrasound probe (104) to accurately position the ultrasound probe (104) over the subject body and obtaining the ultrasound images of the subject body (101). The method (600) comprises positioning (610) the ultrasound probe (104) over the body of the subject body (101) for imaging. The method (600) further comprises capturing (620) a video of the subject (101) and processing the video to generate a torso image of the subject (101) and identify the location of the ultrasound probe (104) on the subject body. Capturing (620) the video of the subject (101) includes using a portable device (102) to obtain the video stream or the images of the subject body. The portable device (102) may be a handheld mobile phone having a camera to capture the video stream or the images of the subject (101), and a display screen.

The method (600) further comprises registering (630) the video to an anatomical atlas to generate a mask of the region of the subject body. The mask may comprise a plurality of sub-regions (560) of the subject body to be imaged and the mask may be superimposed over the torso image. Registering (630) the video may include connecting the portable device (102) to a computer system (103) using a cable or a wireless network and sending the live video stream or images to the computer system (103). The anatomical atlas deployed over the computer system (103) may be configured to process the live stream or the images provided by the portable device (102). The computer system (103) may contain a deep learning (DL) module (113) that may be configured for the body pose detection and generate the torso images of the subject (101) based on the input images received from the portable device (102). An atlas module (114) may be configured to generate a mask of the lung and superimpose the mask over the torso image visible on the mobile screen. The method (600) further includes generating the grid lines by the atlas module (114) over the torso image of the subject (101) to identify the region of the interest for imaging. The atlas module (114) may be further configured to mark a plurality of sub-regions (560) within the grid lines that more accurately define the precise location of the pathologies for imaging. The method (600) further comprises displaying (640) the relative position of the ultrasound probe (104) with respect to a plurality of sub-regions (560) on the subject body to be imaged.

Figure 7:
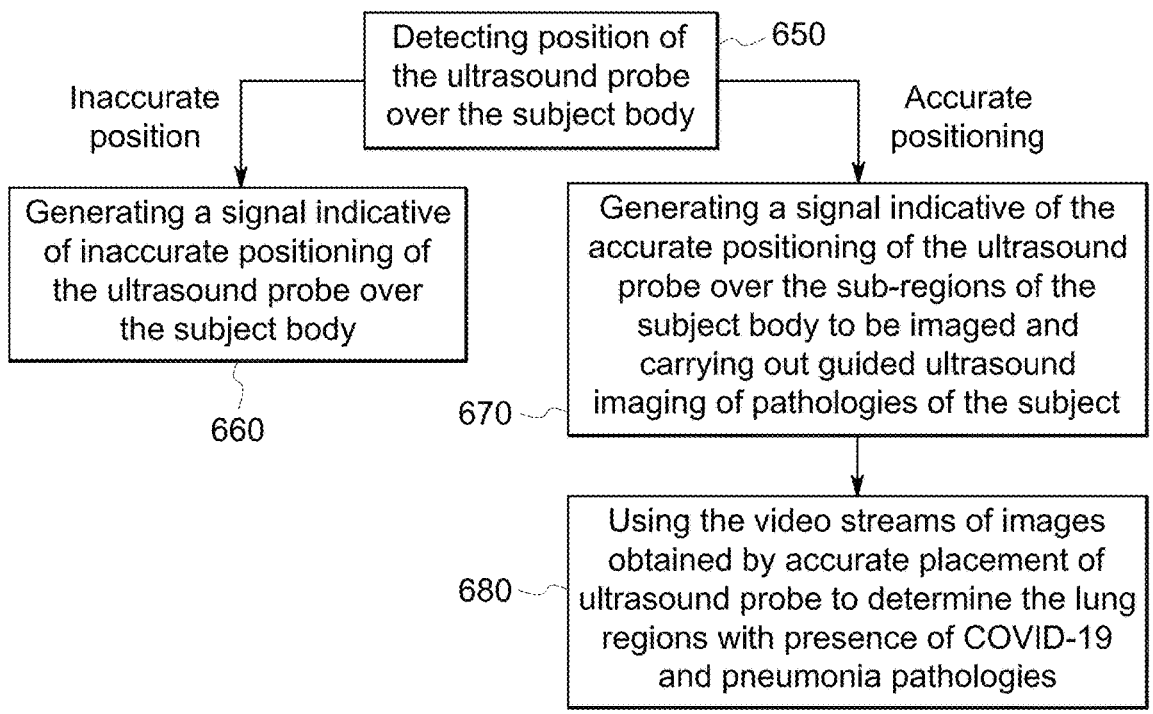
FIG. 7 illustrates a method for analyzing the accurate positioning of the ultrasound probe over the subject body according to an aspect of the disclosure.

As shown in FIG. 7, the method (600) further comprises analyzing (650) the accuracy of the position of the ultrasound probe (104) over the sub-regions (560) of the subject body to be imaged. The computer system (103) may be configured to identify the current location of the ultrasound probe (104) and compare it with the location of the sub-region (560) marked by the atlas module (114). The method (600) further includes generating (660) a signal indicative of the inaccurate positioning of the ultrasound probe (104) over the subject (101). The signal may be an audio-visual signal indicative of the inaccurate position of the ultrasound probe (104) with respect to the marked sub-region (560). Repeated signals may be sent to the operator indicative of the inaccurate positioning of the ultrasound probe (104) until the operator moves the probe to the accurate position or sub-region (560). The ultrasound probe (104) may be moved to an accurate position to sub-region (560) on the subject body (101).

The method (600) further comprises generating (670) a signal indicative of the accurate positioning of the ultrasound probe (104) over the sub-regions (560) of the subject body and carrying out guided ultrasound scanning of the pathologies of the subject (101). Once the ultrasound probe (104) is correctly positioned at the marked sub-region (560), the operator may be instructed by the computer system (103) to scan the subject. The ultrasound images or the video stream of the sub-region (560) of the lung with desired image quality may be obtained to detect the COVID-19 related lung conditions. The method (600) further comprises using (680) the video stream or the images obtained by the accurate placement of the ultrasound probe (104) to determine the lung regions with presence of the COVID-19 and the pneumonia pathologies.

The method (600) may further include employing an artificial intelligence module (113) (Video AI) over the computer system (103) to identify the actual shape of the body and corelate it to the stored images to determine the location of the subject organs during the video imaging by the mobile phone camera. This will supplement the atlas module (114) to more accurately delineate the organs, generate the torso image and the grid lines. This will aid in correctly mapping the subject organs when the subjects (101) with varying body shapes, sizes and height appear for scanning.

The method (600) may further include employing another artificial intelligence module (113) (ultrasound AI) over the computer system (103). The method (600) includes using the ultrasound AI along with the mobile phone camera to detect the position of the ultrasound probe (104) and carrying out scanning. If the ultrasound probe (104) is placed at an inaccurate position, the ultrasound AI (113) may be configured to generate and send a signal indicative of inaccurate positioning of the ultrasound probe (104). For faster detection of the developing COVID-19 conditions in a subject (101), the ultrasound images of the subject (101) may be compared with the similar images to identify the severity of the medical condition. Several ultrasound videos or the images from the various sub-regions (560) of the lung from different subjects (101) may be used to train the ultrasound AI module (113) to analyze the pathologies for the COVID-19 detection.

Figure 8:
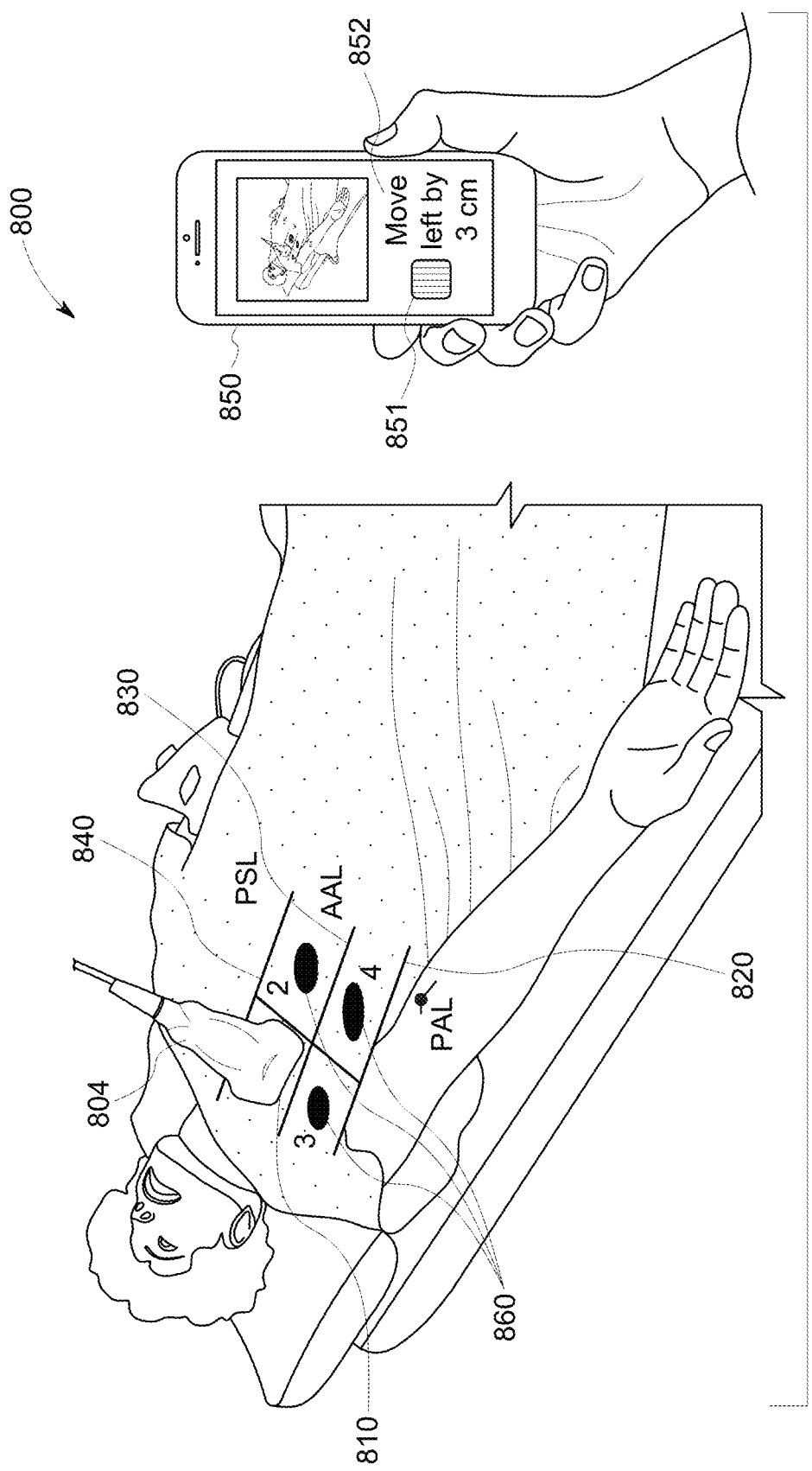
FIG. 8 illustrates a torso image displayed to the operator for imaging according to an aspect of the disclosure.

According to an aspect of the disclosure, FIG. 8 shows a torso image (800) including placement of the ultrasound probe (904) over the subject body (901) to the operator for guided coverage automated detection of pathologies. The operator may be indicated over the screen of the portable device (850) for inaccurate positioning of the ultrasound probe (804) over the subject body (801). The portable device (850) may be a mobile phone. The operator may place the ultrasound probe (804) at any location (810) over the subject body (801). The sub-regions (860) along with the grid lines (820, 830, 840) may be displayed over the mobile phone (850) screen to the operator for imaging. According to an aspect of the disclosure, if the ultrasound probe (804) is not accurately placed at the sub-regions (860) indicated on the torso image (800) on the mobile phone (850), the AI module (113) is configured to generate an audio-visual signal (841) indicative of inaccurate positioning of the ultrasound probe (804) over the sub-regions (860). In one example, the signal may be a red color box indicating inaccurate positioning of the ultrasound probe over the sub-region (860). Although the red color is indicated as an example, any other color scheme may be used for visual display. Further, it is within the scope of the disclosure to use any other mode of signal indication (851) including but not limited to right-wrong sings, human thumb expressions, stop-start button for indicating accuracy of the placement of the ultrasound probe (804). Further, the AI module (113) may be configured to generate a text message (852) about the location of the ultrasound probe (804) and direction in which the ultrasound probe (804) may be moved for accurate positioning of the probe. A text message (852) may be displayed to the operator over the mobile phone (850) screen and the operator will be guided to move the ultrasound probe (804) to an accurate position.

Figure 9:
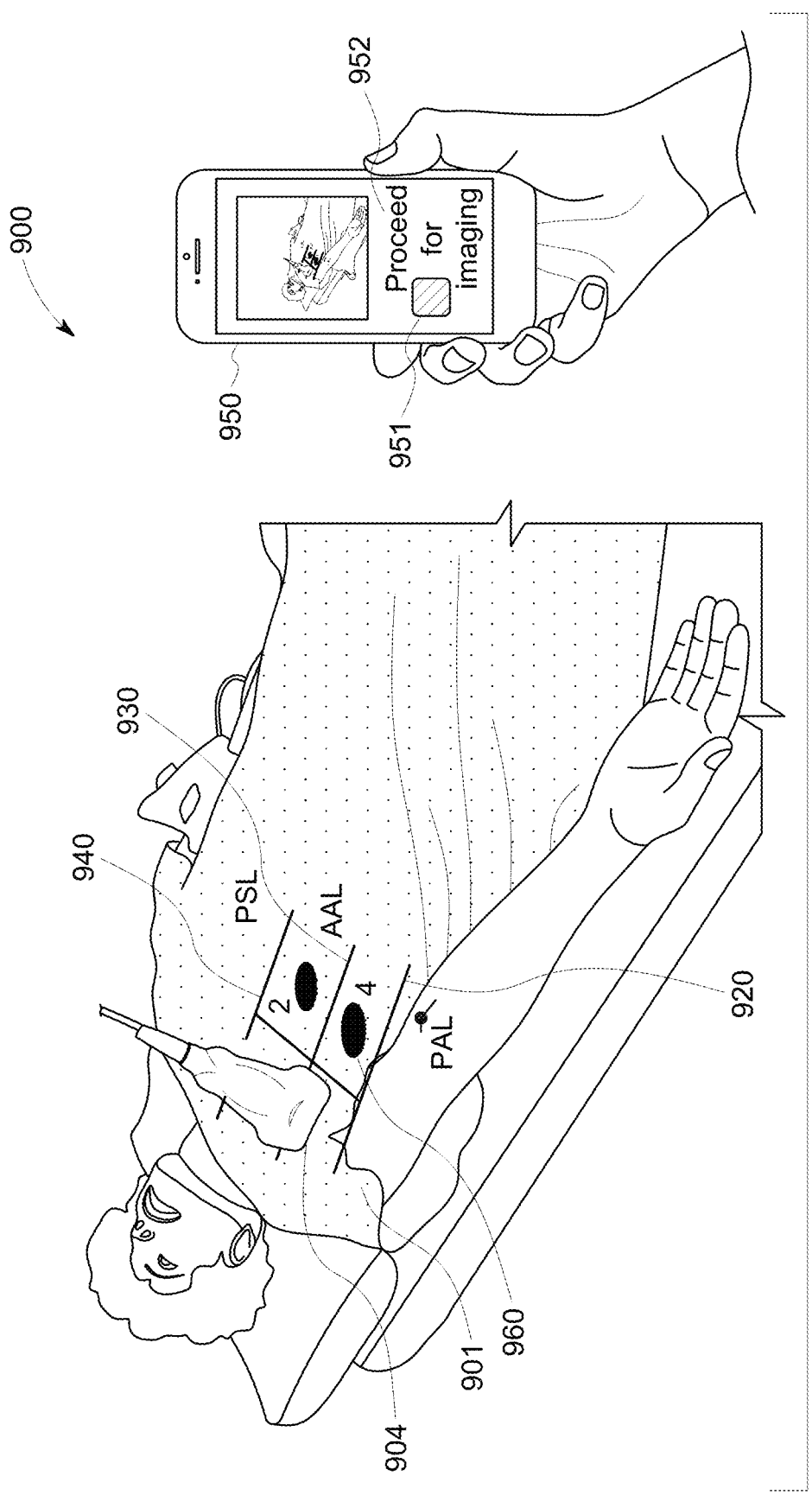
FIG. 9 illustrates a torso image displayed to the operator for guided lung coverage and automated detection according to an aspect of the disclosure.

According to an aspect of the disclosure, FIG. 9 shows a torso image (900) including placement of the ultrasound probe (904) over the subject body (901) for guided coverage and automated detection of pathologies. The torso image (900) may include grid lines (920, 930, 930) and the sub-regions (960) to be imaged may be located within the grid lines (920, 930, 940). When the ultrasound probe (904) is accurately positioned over the identified sub-region (960) over the subject body (901), the AI module (113) may generate a signal indicative of the accurate positioning of the ultrasound probe (904) over the sub-region (960). The operator may be indicated of the accurate positioning of the ultrasound probe (904) over the sub-region (960) over the screen of the mobile phone (950) by a signal. The signal generated by the AI module (113) may be an audio-visual signal. In one example, the signal may be a green color box (951) indicating accurate positioning of the ultrasound probe (904) over the sub-region (960). Although the green color is indicated as an example, any other color scheme may be used for visual display. Further, it is within the scope of the disclosure to use any other mode of signal indication (951) including but not limited to right-wrong sings, human thumb expressions, stop-start button. Further, the AI module (113) may be configured to generate a text message (952) indicating accurate positioning of the ultrasound probe (904) and instruct the operator to carry out imaging. A text message (952) may be displayed to the operator over the mobile phone (950) screen and the operator will be guided to carry out scanning for automated detection of pathologies.

The systems and the methods of the present disclosure may offer a quick diagnosis often required for the COVID-19 infected subjects (101) even when the operator is relatively inexperienced. The systems and the methods of the present disclosure are not only useful for detection of the pathologies within the lung but also for other the pathologies in the subject body. Further, the systems and the methods of the present disclosure are cost effective and may not require multiple sensors for detection of the pathologies or for identifying the accurate position of the ultrasound probe.

This written description uses examples to disclose the invention, including the best mode, and to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for guided coverage and automated detection of pathologies of a subject body, the method comprising:
   positioning an ultrasound probe on a subject's torso;
   capturing a video of the subject body and processing the video to generate a torso image of the subject body and identify a location of the ultrasound probe with respect to the subject body;
   registering the video to an anatomical atlas to generate a mask of a region of the subject body comprising a plurality of sub-regions of the subject body to be imaged and superimposing the mask over the torso image;
   displaying an indicator corresponding to a location of the each of the plurality of the sub-regions on the torso image; and
   displaying a relative position of the ultrasound probe with respect to the indicator corresponding to the location of the each of the plurality of sub-regions of the subject body to be imaged.

2. The method of claim 1, further comprising:
   identifying the relative position of the ultrasound probe over the subject body with respect to the plurality of sub-regions to be imaged; and
   generating a signal indicative of an inaccurate positioning of the ultrasound probe over at least one of the pluralities of the sub-regions.

3. The method of claim 1, further comprising:
   identifying the relative position of the ultrasound probe over the subject body with respect to the plurality of sub-regions to be imaged;
   generating a different signal indicative of an accurate positioning of the ultrasound probe over at least one of the pluralities of the sub-regions of the subject body; and
   carrying out guided ultrasound imaging of pathologies of the subject.

4. The method of claim 1, wherein the region of the subject body is a lung of the subject.

5. The method of claim 1, wherein the sub-regions of the subject body to be imaged comprise a peripheral or a lower region of the lung.

6. The method of claim 1, wherein capturing the video of the subject body comprises using a portable handheld device having a video camera and a display screen.

7. The method of claim 6, wherein the portable handheld device is a mobile phone.

8. The method of claim 1, wherein generating the torso image of the subject body comprises inputting the subject video to a deep learning module trained to detect the subject body position and generate the torso image.

9. The method of claim 1, wherein registering the video to the anatomical atlas comprises using a subset of externally detected landmarks of the subject body by the deep learning module to register with an atlas module.

10. The method of claim 9, wherein the atlas registration provides identification of a pose and an external scale alignment of the subject body.

11. The method of claim 1, further comprising marking a plurality of grid lines on the mask and showing the sub-regions within the grid lines for imaging.

12. The method of claim 1, wherein displaying the relative position of the ultrasound probe with respect to the plurality sub-regions of the subject body further comprises displaying to an operator the sub-regions to be imaged on a mobile phone display and controlling the movement of the ultrasound probe by the operator.

13. The method of claim 2, further comprising employing an artificial intelligence module configured to detect the relative position of the ultrasound probe with respect to at least one of the pluralities of the the sub-regions to be imaged and send the signal indicative of the inaccurate positioning of the ultrasound probe over at least one of the pluralities of the sub-regions of the subject body.

14. The method of claim 13, wherein the artificial intelligence module is further configured to analyze a live stream from the ultrasound probe to detect a presence of infected pathologies in the lung.

15. The method of claim 1, further comprising using a video stream or an image obtained by accurate placement of the ultrasound probe to determine lung regions with presence of a COVID-19 pathology or a pneumonia pathology.

16. A system for guided coverage and automated detection of pathologies of a subject body, the system comprising:
- a portable device comprising a camera and a display configured to acquire a video stream of the subject body;
- an ultrasound probe positioned over a subject's torso and connected to the portable device; and
- a computer system connected to the portable device and configured to receive a plurality of ultrasound images and a video stream of the subject body, wherein the computer system comprises:
  - a processor;
  - a memory connected to the processor;
  - at least one artificial intelligence module deployed over the memory and configured to generate a torso image of the subject body;
  - an atlas module deployed over the memory and configured generate a mask of a region of the subject body comprising a plurality of sub-regions to be imaged and superimpose the mask over the torso image of the subject body;
- wherein the computer system is further configured to display an indicator corresponding to a location of the each of the plurality of the sub-regions on the torso image, and display a relative position of the ultrasound probe with respect to the indicator corresponding to the location of the each of the plurality of sub-regions of the subject body.

17. The system of claim 16, wherein the artificial intelligence module is configured to identify the relative position of the probe with respect to the sub-regions to be imaged and generate a signal if the ultrasound probe is not accurately positioned over at least one of the pluralities of the sub-regions.

18. The system of claim 17, wherein the artificial intelligence module is configured to generate a signal to carry out imaging of the subject if the ultrasound probe is accurately positioned over at least one of the pluralities of the sub-regions.

19. The system of claim 17, wherein the sub-regions comprise a peripheral or a lower region of the lung.

20. The system of claim 17, wherein the artificial intelligence module is configured to analyze a video stream, or an image of the pathologies obtained by the ultrasound probe to detect sub-regions with presence of a COVID-19 or a pneumonia pathology.

21. The system of claim 16, wherein the portable device is a mobile phone.

22. The system of claim 16, wherein the atlas module is configured to mark a plurality of grid lines over the mask and indicate the sub-regions within the grid lines for imaging.

* * * * *